(12) United States Patent
Ehringfeld

(10) Patent No.: US 8,898,038 B2
(45) Date of Patent: Nov. 25, 2014

(54) DETERMINATION OF BEAM PARAMETERS FOR UNFLATTENED PHOTON BEAMS

(75) Inventor: Christian Ehringfeld, Kulmain (DE)

(73) Assignee: Siemens Aktiengesellschaft, Munich (DE)

( * ) Notice: Subject to any disclaimer, the term of this patent is extended or adjusted under 35 U.S.C. 154(b) by 309 days.

(21) Appl. No.: 12/786,158

(22) Filed: May 24, 2010

(65) Prior Publication Data

US 2010/0305905 A1 Dec. 2, 2010

(30) Foreign Application Priority Data

May 28, 2009 (DE) .......................... 10 2009 022 967

(51) Int. Cl.
| | | |
|---|---|---|
| *H03F 1/26* | (2006.01) | |
| *H04B 15/00* | (2006.01) | |
| *A61B 6/00* | (2006.01) | |
| *G21K 1/00* | (2006.01) | |
| *A61N 5/10* | (2006.01) | |

(52) U.S. Cl.
CPC .................................... *A61N 5/1048* (2013.01)
USPC ............................ 702/189; 600/436; 378/145

(58) Field of Classification Search
USPC ............................ 702/189; 600/436; 378/145
See application file for complete search history.

(56) References Cited

U.S. PATENT DOCUMENTS

| | | |
|---|---|---|
| 7,397,904 B2 | 7/2008 | Virshup et al. |
| 2004/0082855 A1* | 4/2004 | Robar et al. ................... 600/436 |
| 2006/0256925 A1 | 11/2006 | Virshup et al. |
| 2007/0086569 A1* | 4/2007 | Johnsen ........................... 378/65 |

FOREIGN PATENT DOCUMENTS

| | | |
|---|---|---|
| DE | WO 2007/098164 | 8/2007 |
| EP | 0253046 A1 | 1/1988 |

OTHER PUBLICATIONS

German Office Action dated Apr. 16, 2010 for corresponding German Patent Application No. DE 10 2009 022 967.1-52 with English translation.
Bayouth, J. E. et al., "Image-Guided Stereotactic Radiosurgery Using a Specially Designed High-Dose-Rate Linac," Medical Dosimetry, vol. 32, No. 2, 2007, pp. 134-141.
Pönisch, F. et al., "Properties of unflattened photon beams shaped by a multileaf collimator," Med. Phys. 33.6, Jun. 2006, pp. 1738-1746.
Sterling, T. D. et al., "Automation of radiation treatment planning," Brit. J. Radiology, vol. 37, No. 439, 1963, pp. 544-550.
Vassiliev, Oleg N. et al., "Dosimetric properties of photon beams from a flattening filter free clinical accelerator," Phys. Med. Biol., 51, 2006, pp. 1907-1917.
UK Search Report dated Sep. 30, 2010 for corresponding UK Patent Application No. GB1008176.8.

* cited by examiner

*Primary Examiner* — John Breene
*Assistant Examiner* — Manuel Rivera Vargas
(74) *Attorney, Agent, or Firm* — Lempia Summerfield Katz LLC

(57) ABSTRACT

A method for determining a beam parameter of an unflattened photon beam generated by an accelerator includes measuring radiation dose values in the plane perpendicular to the beam propagation direction, determining the extension of the unflattened beam using a definition of the beam extension of a flattened beam. The method also includes normalizing the radiation dose values, such that essentially the same value for the extension of the unflattened beam is obtained as would be obtained if the beam was flattened and determining the beam parameter of the unflattened beam using a beam parameter definition of a flattened beam.

8 Claims, 4 Drawing Sheets

FIG 5

| squ. FS [cm²] | DCAX [%] |
|---|---|
| 0 x 0 | 100 |
| 1 x 1 | 100 |
| 5 x 5 | 105 |
| 10 x 10 | 115 |
| 15 x 15 | 130 |
| 20 x 20 | 145 |
| 25 x 25 | 160 |
| 30 x 30 | 175 |
| 35 x 35 | 190 |
| 40 x 40 | 200 |

DETERMINATION OF BEAM PARAMETERS FOR UNFLATTENED PHOTON BEAMS

This application claims the benefit of DE 10 2009 022 967.1 filed May 28, 2009, which is hereby incorporated by reference.

BACKGROUND

The present embodiments relate to a method and apparatus for determining a beam parameter of an unflattened photon beam generated by an accelerator.

In medical engineering, accelerators are used to generate beams. Linear accelerators (e.g., linac) are typically used, generating electrons or, as secondary or deceleration radiation, photons for the beam used. The generated beam can be used for both diagnostic and therapeutic purposes.

The beam intensity of the generated beam is generally not regular. To achieve a regular intensity over the cross section of the beam used, flattening filters are used. The flattening filters are tailored to the characteristic intensity distribution of the beam so that a regular beam intensity is achieved over the cross-sectional region of the beam due to radiation or photon absorption. Since the unflattened beam generally produces the maximum intensity in the center of the beam and has an intensity characteristic that diminishes continuously with distance from the center, flattening filters may be configured so that the filters have the greatest absorption in the center of the beam, and absorption capacity decreases with distance from the center of the beam. Such flattening filters are disclosed, for example, in EP 0253 046 A1 (e.g., for therapeutic applications) and US 2006/0256925 A1 (e.g., for diagnostic applications).

Attempts have been made during the therapeutic deployment of accelerators for photon generation to dispense with the flattening filter during radiation. Unflattened beams have a considerably higher dose rate than flattened beams. The flattened beam typically has a maximum of 500 monitor units (MU) per minute, with the unflattened beam having a significantly higher range with respect to maximum value (e.g., currently up to 2000 MU/min). "Monitor units" is an internal designation for the output of a linac. Calibration takes place, such that in reference conditions (e.g., defined distance, measuring depth, and field size) an MU corresponds to the dose of 0.01 Gy (Gray). Since very high dose rates (e.g., several thousand MU) are used in applications such as stereotaxy and intensity modulated radiotherapy (IMRT), for example, treatment time is significantly reduced when unflattened beams are used. Fields of smaller extension (e.g., field size) are used for stereotaxy and IMRT. With the standard radiation output of flattened beams, the time required to apply a quantity of radiation for the treatment would therefore be considerable. The time to apply the quantity of radiation is significantly reduced by the increase in radiation intensity associated with the removal of the flattening filter.

The use of unflattened photon beams for therapeutic purposes is also described in Bayouth J. E. et al. "Image-guided stereotactic radiosurgery using a specially designed high-dose-rate LINAC." *Medical Dosimetry.* 32.2 (2007): 134-41 and Pönisch F. et al. "Properties of unflattened photon beams shaped by a multileaf collimator." *Med. Phys.* 33.6 (2006) 1738-46. Bayouth et al. argue that the use of unflattened beams also results in a reduction in the overall quantity of radiation absorbed by the patient (see p. 136).

Unflattened beams may be described or classified for use. Parameters for beam description have been defined for flattened beams and are used universally in accelerator technology. These parameters are, for example, the parameters field size, penumbra, symmetry and flatness. Since the definition of such parameters was stipulated for flattened beams, the values obtained according to the definitions of the parameters do not provide the same information content for unflattened beams as for flattened beams. Using these parameter definitions for unflattened beams results in parameter values of unflattened and flattened beams no longer being compared at least to some degree. Parameter values of unflattened beams are also no longer directly comparable with a different beam extension. A complex conversion may be used for comparison, as is attempted, for example, by F. Pönisch et al. in "Properties of unflattened photon beams shaped by a multileaf collimator."

SUMMARY AND DESCRIPTION

The present embodiments may obviate one or more of the drawbacks or limitations in the related art. For example, in one embodiment, a method and apparatus for simplified parameter determination for unflattened photon beams may be specified.

Parameter definitions for flattened beams may be used with unflattened beams when radiation dose values are scaled as a function of field extension.

According to the present embodiments, a beam parameter of an unflattened photon beam generated by an accelerator (e.g., by a linac) is determined. In one embodiment of a method for beam parameter determination, radiation dose values are measured in a plane perpendicular to the beam propagation direction. The beam propagation direction may be determined by the accelerator used. A definition of the beam extension (e.g., field size) of a flattened beam is used. The definition of the beam extension is used to normalize or rescale the measured radiation dose values. This normalization is conducted in such a manner that the value that would be obtained for the extension of the flattened beam is essentially obtained for the extension (field size) of the unflattened beam. Dose values of the flattened beam for normalization may be determined beforehand in a measurement. In one embodiment described below, a fit function is used for normalization. The term "essentially" takes into account inaccuracies due to the fit method. Normalization may include multiplying the radiation dose values (e.g., given as a percentage of the maximum dose) by a factor. According to the present embodiments, the radiation dose is set so that essentially the same field extension is obtained as for a flattened beam, and the values for the field extension for the flattened and unflattened beams essentially correspond (when using the same standard definition for the flattened beam). This procedure makes use of the fact that the extension of beams that can be used for therapeutic purposes is limited by collimators, and the definition of the extension of the flattened beam is generally selected so that the extension defined by the collimator is obtained within the context of the accuracy that is of relevance for radiation. The term "essentially" may also be that normalization brings about a correspondence within the context of the accuracy of the parameter "field size" for beam characterization.

As a result of normalization, beam parameter definitions for the flattened beam may be used to determine beam parameters of the unflattened beam. A beam parameter may be beam extension or field size, for example, which essentially corresponds structurally to the extension of a flattened beam. Other beam parameters that provide meaningful information about beam characteristics and can be compared with corresponding beam characteristics of flattened beams may also be determined for the unflattened beam (e.g., penumbra and symmetry).

In the present embodiments, parameters, which provide meaningful information about the beam without further adjustment and can be compared with corresponding parameters of unflattened beams, are determined. In one embodiment, scaling values for normalization for a number of values for beam extension are determined, and the scaling values are used to generate a fit curve for scaling values as a function of the field extension. This scaling function formed by a fit may be used to normalize radiation dose values for any field extension values. The scaling function may be calculated once; when the scaling function is applied, the unflattened beam may not be compared with the flattened beam.

The drop of an isodose (e.g., a percentage distribution of the dose) to 50% of the maximum dose, for example, is used as a definition of beam extension. The radiation dose values may be normalized to a percentage value (e.g., to some degree greater than 100%), such that a drop of the isodose to 50% results essentially in the same positions to those for the flattened beam.

The present embodiments also include an apparatus or apparatus elements for implementing the method according to the present embodiments. The apparatus includes a measuring facility for measuring radiation dose values in a plane perpendicular to the beam propagation direction. Standard commercially available measuring apparatuses such as ionization chambers, for example, may be used as the measuring facility. The apparatus also includes a computer unit configured to normalize the radiation dose values according to the present embodiments. The computer unit may be a PC or workstation, for example. In one embodiment, the computer unit may be used for additional processes (e.g., control or regulation of medical facilities used).

BRIEF DESCRIPTION OF THE DRAWINGS

FIG. 5 shows a table of scaling values for establishing the fit function.

DETAILED DESCRIPTION OF THE DRAWINGS

Figure 1:
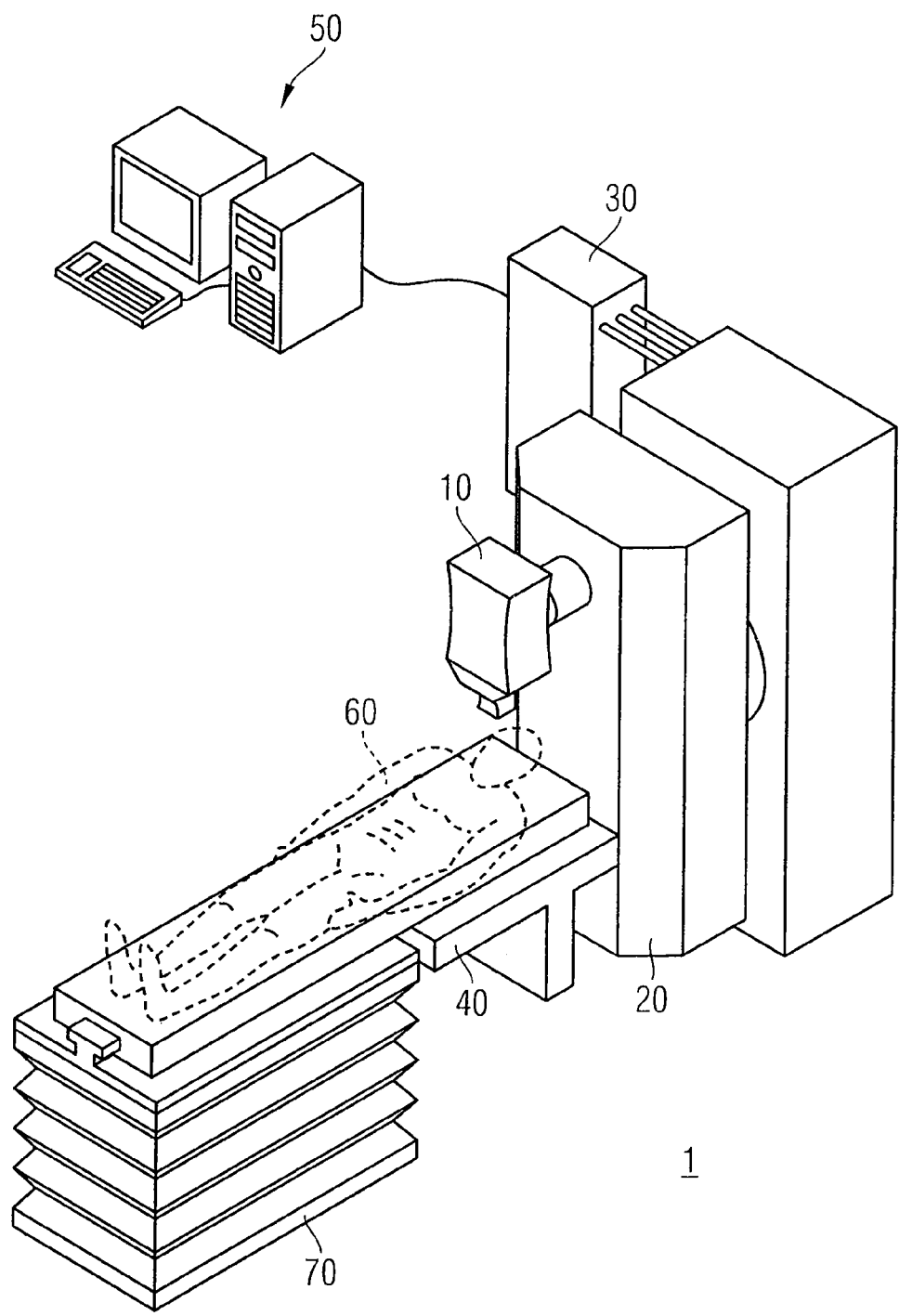
FIG. 1 shows a treatment room with an accelerator.

FIG. 1 shows equipment elements of a treatment room. The treatment room 1 includes a housing of a linear accelerator 10, which is secured to a rotatable gantry 20. An energy supply is provided by way of a unit 30, which is connected to an input and a control system 50. The control system 50, for example, also supplies the computation resources for implementing the present embodiments. The treatment room also includes a patient table 70 and a patient 60 positioned on the patient table 70 for treatment.

Figure 2:
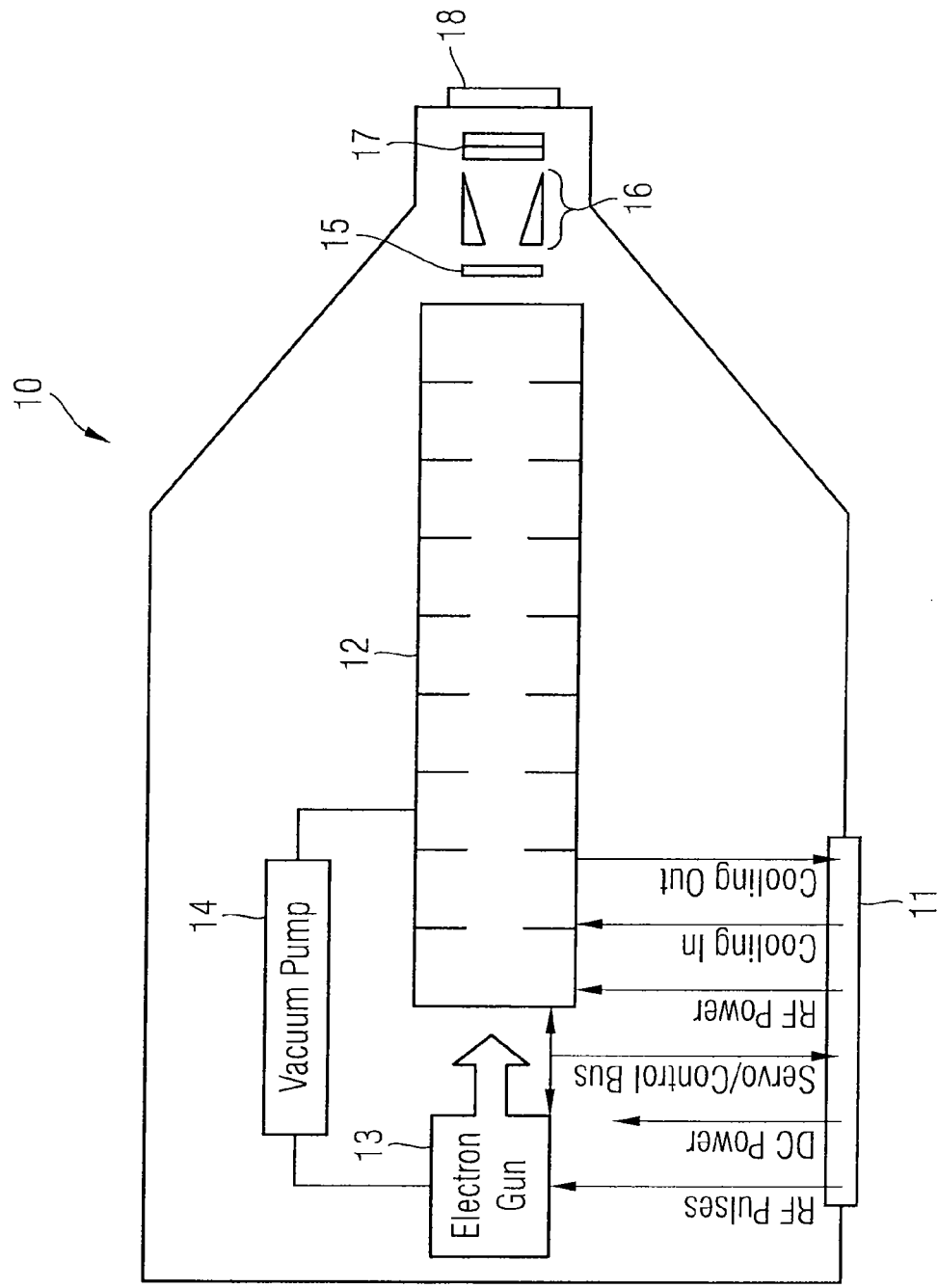
FIG. 2 shows a schematic diagram of a linear accelerator.

FIG. 2 shows a schematic diagram of the structure of a linear accelerator. The linear accelerator includes a control interface 11, a system 12 for directing and accelerating electrons, an electron source 13, a vacuum pump 14, a target 15, a collimator 16, a dosimeter 17 and securing brackets 18. The housing 10 of the linear accelerator may be coated with a material that shields against magnetic fields and radiation to protect inner elements of the housing. Electrons generated by the electron source 13 (e.g., an electron beam) are sent to the target 15 by the routing system 12. The target 15 may be made of a material with a high atomic weight (e.g., gold or tungsten). As the electron beam strikes the target 15 and decelerates, a photon beam having an appropriate energy spectrum for radiotherapy is generated. The securing brackets 18 may be used, for example, to attach a flattening filter. The present embodiments may be used for applications where no flattening filter is provided.

Beam parameters of a flattened beam (e.g., produced by the linear accelerator of FIG. 2) include field extension (e.g., field size), penumbra, symmetry and flatness. A large number of the beam parameters, which were originally defined for flattened beams, may also be applied with the same definition for unflattened beams if normalization according to the present embodiments takes place. One parameter that may be used for the unflattened beam is, for example, field extension or field size. For flattened beams, the field extension or the field size may be defined by the drop to 50% of maximum intensity (e.g., 50% isodose). One parameter that may also be used is the penumbra, which may be defined as the interval between the 20% and 80% intensity values or isodoses (i.e., the penumbra parameter measures how quickly the field drops from 80% intensity to 20% intensity or how sharply the field extension is defined, and thus, also provides a measure of accuracy of the value for field extension). The penumbra parameter is also a measure of accuracy, which may be used for the comparison with the field size of the flattened field described in FIG. 3. The normalization according to the present embodiments may be carried out in such a manner that a correspondence error is not greater than the value for the penumbra parameter of the flattened beam. The term "essentially" with respect to the correspondence of the field extension of the flattened beam and the normalized unflattened beam may be defined correspondingly. Symmetry may be $100\% \times |a-b|/|a+b|$, where a is the area to the left of a central axis and b is the area to the right of the central axis. These areas are limited by the central axis and the 50% field boundary. Symmetry is also a characteristic that is relevant for unflattened beams. In contrast, the flatness or homogeneity parameter, for example, may have little meaning for unflattened beams.

Figure 3:
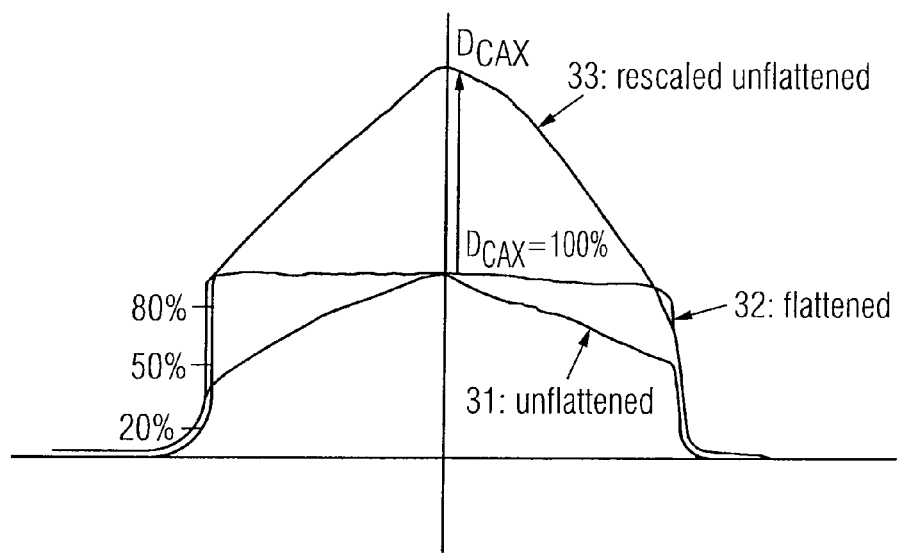
FIG. 3 shows normalization of radiation dose values.

FIG. 3 shows how normalization according to the present embodiments may be undertaken. FIG. 3 shows 3 curves (e.g., 31: unflattened, 32: flattened, and 33: resealed unflattened), which illustrate the percentage values of beam intensity as a function of position. The central vertical axis (e.g., the y-axis) is the central axis of the beam and where the beam has maximum intensity. The maximum intensity value is shown as $D_{cax}$ in FIG. 3. Curve 32 is a standard representation of a flattened beam and is normalized to 100% maximum. In the horizontal interval, the intensity values on both sides of the vertical axis are essentially constant before dropping very quickly in a transition region to low percentage values. This approximate constancy of intensity is lost with the unflattened beam (e.g., curve 31), which is shown below curve 32. Curve 31 is normalized to 100% maximum and shows a constant drop at the sides with increasing distance from the vertical axis, the drop accelerating and becoming a fast drop to zero in a peripheral region. There is also a fast drop in the peripheral region for curves for flattened beams, the peripheral region essentially being defined by an aperture of a collimator. Definitions for the flattened beam cannot be used directly due to the drop between the maximum value and the peripheral region, which does not occur with flattened beams.

According to the present embodiments, the curve for the unflattened beam 31 is multiplied by a scaling factor, such that when the definition for field extension for the flattened beam is applied, a corresponding field extension results for the unflattened beam. In FIG. 3, curve 33 is thus obtained, having values higher than 100%. When the definition for the extension of a flattened beam (e.g., the drop to 50% of the isovalue) is applied to the normalized curve, essentially the same value results for the extension as for the flattened beam, as shown in FIG. 3. FIG. 3 illustrates that the drop of the unflattened curve 31 on the left is greater than on the right. The scaling factor may be defined, such that for the x-value at which the flattened curve 32 drops to 50% on the left of the vertical axis, the rescaled curve 33 has the same value as the flattened curve 32. Normalization or rescaling is carried out by making one point (50% point) on the curves correspond.

Figure 4:
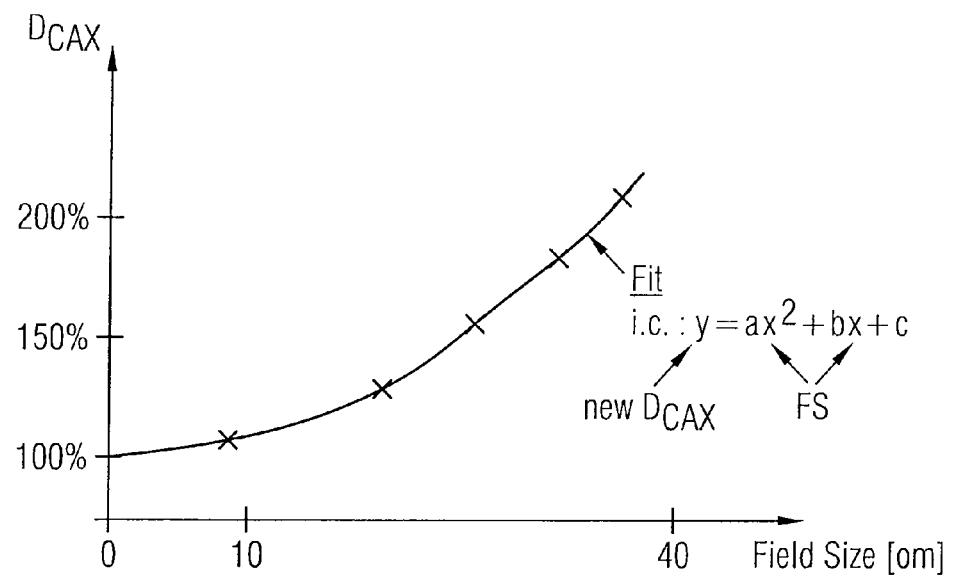
FIG. 4 shows a plot of a fit function.

The procedure illustrated in FIG. 3 may be repeated for different field sizes. In the table shown in FIG. 5, for example, scaling values are shown as a function of field extension. These points may be used to plot a fit curve, as shown in FIG. 4. As illustrated in FIG. 4, a second degree polynomial was selected, (e.g., three parameters of the fit curve were determined by way of the fit). This curve, which shows the maximum percentage value of the resealed curve as a function of field size, may be used to obtain the scaling value very quickly for any field sizes. The present embodiments may be applied for square form beams. Rectangular field forms may, however, be related to equivalent square field forms so the method according to the present embodiments may also be applied (e.g., see Sterling et al. "Automation of radiation treatment planning." *Brit. J. Radiol.* 37 (1964): 544-50.). In one embodiment, an interpolation between selected field sizes may be used instead of a fit function.

In one embodiment, other fit functions may be used to create a curve according to FIG. 4. In another embodiment, different scaling values from those listed in the table of FIG. 5 may be used.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for determining a beam parameter of an unflattened photon beam generated by an accelerator, the method comprising:
   measuring radiation dose values of the unflattened photon beam in a plane perpendicular to a beam propagation direction;
   rescaling, by a computer unit, the measured radiation dose values based on a definition of a beam extension of a flattened beam, the beam extension of the flattened beam extending in a direction perpendicular to the beam propagation direction and corresponding to a field size of the flattened beam, the rescaling comprising setting the measured radiation dose values such that a same value is obtained for the extension of the unflattened photon beam as would be obtained if the beam was flattened; and
   determining the beam parameter of the unflattened photon beam using a beam parameter definition of the flattened beam based on the rescaling.

2. The method as claimed in claim 1, wherein the definition for the beam extension of the flattened beam is the drop of an isodose to 50%, and
   wherein rescaling the measured radiation dose values comprises rescaling a maximum radiation dose to a percentage value, such that the drop of the isodose to 50% essentially results at one position that is the same to that of the flattened beam.

3. The method as claimed in claim 2, wherein resealing the measured radiation dose values comprises:
   determining scaling values for resealing for a number of values for beam extension;
   forming a scaling function for resealing that is a function of extension by a curve fit or by interpolation of the values for beam extension; and
   resealing the measured radiation dose values using the scaling function.

4. The method as claimed in claim 2, wherein determining the beam parameter comprises determining beam extension, penumbra or symmetry.

5. The method as claimed in claim 1, wherein resealing the measured radiation dose values comprises:
   determining scaling values for resealing for a number of values for beam extension;
   forming a scaling function for resealing that is a function of extension by a curve fit or by interpolation of the values for beam extension; and
   resealing the measured radiation dose values using the scaling function.

6. The method as claimed in claim 5, wherein determining the beam parameter comprises determining beam extension, penumbra or symmetry.

7. The method as claimed in claim 1, wherein determining the beam parameter comprises determining beam extension, penumbra or symmetry.

8. An apparatus for determining a beam parameter of an unflattened photon beam generated by an accelerator, the apparatus comprising:
   a measuring facility operable to measure radiation dose values of the unflattened photon beam in a plane perpendicular to a beam propagation direction; and
   a computer unit configured to:
      rescale the measured radiation dose values, such that essentially a same value is obtained for an extension of the unflattened photon beam as would be obtained for an extension of a flattened beam, the extension of the flattened beam extending in a direction perpendicular to the beam propagation direction and corresponding to a field size of the flattened beam; and
      determine the beam parameter of the unflattened photon beam using a beam parameter definition of the flattened beam based on the rescale.

* * * * *